(12) United States Patent
Li et al.

(10) Patent No.: US 10,487,421 B2
(45) Date of Patent: Nov. 26, 2019

(54) REINFORCED ELECTROSPUN FIBROUS MEMBRANE AND PREPARATION METHOD THEREOF

(71) Applicant: Medprin Regenerative Medical Technologies Co., Ltd., Guangzhou (CN)

(72) Inventors: Guangyao Li, Guangdong (CN); Kunxue Deng, Guangdong (CN); Yaya Yang, Guangdong (CN); Yuyu Yuan, Guangdong (CN)

(73) Assignee: Medprin Regenerative Medical Technologies Co., Ltd., Guangzhou (CN)

( * ) Notice: Subject to any disclaimer, the term of this patent is extended or adjusted under 35 U.S.C. 154(b) by 0 days.

(21) Appl. No.: 15/736,997

(22) PCT Filed: Jun. 16, 2016

(86) PCT No.: PCT/CN2016/086053
§ 371 (c)(1),
(2) Date: Dec. 15, 2017

(87) PCT Pub. No.: WO2016/202281
PCT Pub. Date: Dec. 22, 2016

(65) Prior Publication Data
US 2018/0171510 A1 Jun. 21, 2018

(30) Foreign Application Priority Data
Jun. 17, 2015 (CN) .......................... 2015 1 0336228

(51) Int. Cl.
*A61F 2/08* (2006.01)
*D04H 1/728* (2012.01)
(Continued)

(52) U.S. Cl.
CPC ............. *D01D 5/0007* (2013.01); *A61F 2/08* (2013.01); *D01D 5/00* (2013.01); *D04H 1/42* (2013.01); *D04H 1/728* (2013.01); *A61L 27/58* (2013.01)

(58) Field of Classification Search
CPC ....................................................... D04H 1/728
See application file for complete search history.

(56) References Cited

U.S. PATENT DOCUMENTS

| 2011/0014153 A1* | 1/2011 | Derwin ..................... A61F 2/08 424/85.1 |
| 2012/0165957 A1* | 6/2012 | Everland ............... A61F 2/0045 623/23.72 |

(Continued)

*Primary Examiner* — Megan Y Wolf
(74) *Attorney, Agent, or Firm* — Sheppard Mullin Richter & Hampton LLP (57) ABSTRACT

The present disclosure discloses reinforced electrospun fibrous membranes and preparation methods therefor. The reinforced electrospun fibrous membranes can include an electrospun fibrous membrane body and a plurality of reinforcing thread sets fixed to the electrospun fibrous membrane body through holes thereon, wherein any two of the plurality of reinforcing thread sets are parallel to each other; each of the reinforcing thread sets comprises a starting end and a terminal end, both being connected to an edge of the electrospun fibrous membrane body; each of the reinforcing thread sets comprises at least one reinforcing fibrous thread consisting of a main thread and an auxiliary thread respectively arranged at a front side and a bottom side of the electrospun fibrous membrane body and configured to interlace each other at the through hole. By providing reinforcing thread sets on the electrospun fibrous membrane body to impart the electrospun fibrous membrane with a greater mechanical property, the mechanical strength required for the movement of the tissue is ensured, and the electrospun fibrous membrane is easy to be folded or rolled into other shapes. The electrospun fibrous membrane body may be (Continued)

made of degradable materials, which are gradually degraded and absorbed in the process of inducing new tissue formation, thereby providing space for the formation of new tissues.

19 Claims, 4 Drawing Sheets

(51) Int. Cl.
*D01D 5/00* (2006.01)
*D04H 1/42* (2012.01)
*A61L 27/58* (2006.01)

(56) References Cited

U.S. PATENT DOCUMENTS

2015/0230918 A1* 8/2015 Detamore ................ A61F 2/04
                                                                  623/9
2018/0296316 A1* 10/2018 Thian ...................... A61L 27/18

\* cited by examiner a b

REINFORCED ELECTROSPUN FIBROUS MEMBRANE AND PREPARATION METHOD THEREOF

CROSS REFERENCE TO RELATED APPLICATIONS

The present application is the U.S. national stage application of International Application PCT/CN2016/086053, filed Jun. 16, 2016, which claims priority to Chinese Patent Application No. 201510336228.2, filed Jun. 17, 2015, the contents of which are incorporated herein by reference in their entireties in the present disclosure.

TECHNICAL FIELD

The present invention belongs to the biomedical field, specifically relates to reinforced electrospun fibrous membranes and preparation methods thereof.

BACKGROUND

Braided membranes are common products for repair of human soft tissues, which have the advantage of high mechanical strength, but have higher hardness and poor biocompatibility and are prone to cause side effects such as inflammation and proliferation after implantation. More recently, researchers have developed electrospun fibrous membranes featuring softness and ease of cell growth therein to substitute for braided membranes. Although the biocompatibility of electrospun fibrous membranes is higher than that of braided membranes and thus they can better repair soft tissues, the electrospun fibrous membranes lack strength, and thus for some of the parts requiring higher mechanical properties, they cannot meet the application requirements.

In the prior art, an electrospun fibrous membrane and a braided membrane are used in combination to improve the mechanical property of the electrospun fibrous membrane; however the two kinds of membranes are significantly different in structure and are easy to be separated from each other, and the braided membrane has a great hardness and takes up a large proportion in a composite membrane, so that the composite membrane is hard to be cut and folded and is unable to achieve a desirable effect of repairing products.

SUMMARY

Technical Problems

An inventive objective of the present invention is to overcome the deficiencies in the prior art by providing a reinforced electrospun fibrous membrane featured in softness, good biocompatibility and ease of cell growth therein, and imparting the membrane with a stable mechanical property of desirable tissue repair products; and the reinforced electrospun fibrous membrane has excellent adhesiveness, that is, the two materials in the resulting membrane are well adhered and not separated from each other, without any discomfort after implanted into the human body.

Another objective of the present invention is to provide a method of preparing the reinforced electrospun fibrous membrane.

Means for Solving the Problems

The present invention provides a reinforced electrospun fibrous membrane, comprising: an electrospun fibrous membrane body and a plurality of reinforcing thread sets fixed to the electrospun fibrous membrane body via through holes thereon, wherein any two of the reinforcing thread sets are parallel to each other; each of the reinforcing thread sets comprises a starting end and a terminal end, both being connected to an edge of the electrospun fibrous membrane body; each of the reinforcing thread sets comprises at least one reinforcing fibrous thread consisting of a main thread and an auxiliary thread respectively arranged at both sides of the electrospun fibrous membrane body and configured to interlace each other at the through hole.

The reinforced electrospun fibrous membrane means an electrospun fibrous membrane which is reinforced, and the electrospun fibrous membrane refers to an electrospun membrane well known by a person skilled in the art.

"Interlacing" and "crossing" are terms for describing the relationship between threads. When thread A and thread B are interlaced, threads A and B are intertwined at the junction of the two threads; when thread A and thread B are crossed, threads A and B are not wined at the junction of the two threads.

In the present invention, "each" means each (group); "any" means any one (group) or multiple (groups).

In the above manner reinforcing fibrous threads are bonded to an electrospun fibrous membrane body, and all of the reinforcing thread sets are distributed in parallel to form the same orientation, so that the mechanical property of the electrospun fibrous membrane body in the extension direction of the reinforcing fibrous threads can be significantly enhanced. Compared with the common method of reinforcing an electrospun membrane by combining a braided membrane with an electrospun membrane in the art, a product obtained by reinforcing the electrospun fibrous membrane via reinforcing thread sets does not have a problem of excessively high hardness and is easy to be folded or rolled into other shapes; meanwhile, although the way of combining reinforcing thread sets with the electrospun fibrous membrane body can enhance the mechanical property, the introduction of the reinforcing thread sets causes reinforcing fibrous threads to be elevated or bulged on the surface of the electrospun fibrous membrane body due to the rigidity and elasticity of filaments, so that the reinforcing fibrous threads can hardly be adhered to and integrated with the electrospun fibrous membrane body. When the reinforcing fibrous threads are not well adhered to the electrospun fibrous membrane body, common defects in the prior art occur, for example, the electrospun fibrous membrane body tends to be torn when pulled; a reinforcing fibrous thread composed of two or more filaments cannot be made into strands; the reinforcing fibrous thread is liable to be detached or even extracted from the electrospun fibrous membrane body; it is inconvenient for clinical application, and so on.

Both of the main thread and the auxiliary thread can be made of filaments. The auxiliary thread is subjected to twisting treatment at a twist of 10-100. By subjecting the auxiliary threads to twisting treatment, reinforcing fibrous threads can be well adhered to an electrospun fibrous membrane body to achieve good adhesiveness. At the same time, a twist of the auxiliary thread has an important influence on adhesiveness. If a twist of the auxiliary thread is too high, the adhesiveness will instead decrease and the processing becomes difficult; if a twist of the auxiliary thread is too low, an improvement over the adhesiveness is not obvious. Therefore, the control of a twist of the auxiliary thread in a suitable range can achieve better adhesiveness, so that the resulting reinforced electrospun fibrous membrane or its article when implanted in the human body provides a higher degree of comfort. Accordingly, it is preferable that the auxiliary thread has a twist of 10-100.

Filaments constituting the main thread and the auxiliary thread also have an effect on an improvement over adhesiveness of reinforcing fibrous threads to an electrospun fibrous membrane body. The greater a diameter of a filament is, the higher its strength is, but its adhesiveness decreases after it is fixed to an electrospun fibrous membrane body. When a diameter of the filament exceeds a certain value, the above defect after combination is more obvious, and foreign body sensation increases after implanted in the human body. Accordingly, the present invention allows reinforcing fibrous threads to get a better adhesiveness after fixed to the electrospun fibrous membrane body by controlling a diameter of the filament in a range of 0.01 mm or less.

The main thread may or may not be subjected to the twisting treatment. After the twisting treatment, the main thread can be improved in loading capacity.

In order to provide a better reinforcing effect, it is preferable that each of main threads or auxiliary threads is made of at least two filaments; further, a diameter of the filament is 0.01 mm or less.

Besides, a reinforcing effect can be enhanced by increasing the quantity of the reinforcing fibrous threads in the same reinforcing thread set. Preferably, any one of the reinforcing thread sets contains at least two reinforcing fibrous threads.

Preferably, a pitch between two adjacent through holes in one reinforcing thread set is from 5 to 15 mm. Such a configuration helps to keep adhesiveness of reinforcing fibrous threads to an electrospun fibrous membrane body.

All of the reinforcing thread sets extend in the same direction, so the mechanical property is greatly increased in this extension direction. Preferably, the extension direction of the reinforcing thread sets is the same as the length or width direction of the electrospun fibrous membrane body.

The fiber distribution of the electrospun fiber membrane body may be non-oriented or oriented to some extent. Subjecting the fiber distribution to orientation can improve the mechanical property of this orientation direction and is conducive to oriented growth of tissue after implantation into body, and is more suitable for oriented tissue repair. Preferably, the fiber distribution of the electrospun fibrous membrane body is oriented, and the extension direction of the reinforcing thread set is the same as the fiber orientation direction of the electrospun fibrous membrane body.

Preferably, the electrospun fibrous membrane body has a thickness of 0.2 to 2 mm.

Preferably, the reinforced electrospun fibrous membrane is provided with 2 to 20 reinforcing thread sets.

Preferably, a distance between two adjacent reinforcing thread sets is from 2 to 25 mm.

Preferably, through holes are configured on the electrospun fibrous membrane body between two reinforcing thread sets. The configuration of through holes is more favorable for exchange of nutrition between two sides of the fibrous membrane body to promote cambium to grow in.

The filament material constituting the main thread or the auxiliary thread according to the present invention is preferably a material that is medically implanted in humans. More preferably, the filament is a silk fiber, a polyester fiber, an ultra high molecular weight polyethylene fiber, a polylactic acid fiber or a polycaprolactone fiber, wherein the ultra high molecular weight polyethylene fiber (UHMWPE for short) is a fiber that is spun out of ultra high molecular weight polyethylene and well known by a person skilled in the art.

Preferably, the electrospun fibrous membrane body is composed of degradable materials.

Preferably, the degradable material is any one of or a mixture of two or more of polyurethane, polylactic acid, polycaprolactone, polyglycolic acid, polymethylmethacrylate, chitosan, lactic acid-glycolic acid copolymer, alginic acid, alginate, collagen, gelatin, chondroitin, hyaluronic acid, fibrin, and modified cellulose.

In more favor of tissue repair, it is preferable that the electrospun fibrous membrane body contains a bioactive factor.

Preferably, the bioactive factor is any one of or a mixture of two or more of a platelet growth factor, a basic fibroblast growth factor, a bone growth factor, a vascular endothelial growth factor, a connective tissue growth factor and a glial growth factor.

An entire shape of the reinforcing thread sets may be in various linear shapes, and preferably, each of the reinforcing thread sets is in a straight line as a whole.

A method of preparing the reinforced electrospun fibrous membrane comprises steps of:

S1: preparing for an electrospun fibrous membrane body;
S2: preparing a main thread and an auxiliary thread;
S3: fixing the main thread and the auxiliary thread to the electrospun fibrous membrane body by means of sewing.

More preferably, the main thread as an upper thread and the auxiliary thread as a bottom thread are fixed to the electrospun fibrous membrane body by means of sewing.

Preferably, the step S1 comprises steps of:

S11: preparing an electrospun solution, in which a polymer has a concentration of 5 to 20 percent by mass/volume;

S12: setting ranges of parameters for electrostatic spinning as below: spinning voltage: 10 kv to 50 kv; solution propulsion velocity: 2.5 mL/h to 10 mL/h; receiving distance: 10 cm to 30 cm; rolling speed of a receiver: 400 to 2000 r/min; subjecting the aforesaid electrospun solution to electrostatic spinning to obtain the electrospun fibrous membrane body. The temperature and humidity during the electrostatic spinning may be referred to those necessary for conventional operations.

Sewing is a good way to fix the reinforcing thread sets to the electrospun fibrous membrane body, which can be performed by a common existing sewing machine (for example, a sewing machine for a domestic or garment factory).

After a sewing machine is selected, some conditions during the sewing are generally confirmed, such as a size of the formed through hole and a distance between the through holes and so on.

Preferably, bioactive factors are sprayed while performing electrostatic spinning.

Use of the reinforced electrospun fibrous membrane in the preparation of materials for repair of human bodies is provided.

Bionic ligaments or bionic tendons made of the reinforced electrospun fibrous membranes are provided.

A bionic ligament made of the reinforced electrospun fibrous membranes is obtained by rolling the reinforced electrospun fibrous membranes into a tubular shape and then securing them by sewing. In the case where the main body of the reinforced electrospun fibrous membrane constituting bionic ligaments is configured with through holes, it is more advantageous for the tissue to grow into the tubular implant as soon as possible and increase the exchange of materials inside and outside the tubular body.

Preferably, in the above bionic ligament, the through holes are configured in the electrospun fibrous membrane body between two reinforcing thread sets.

Advantageous Effects

Compared with the prior art, the present invention has the following advantageous effects:

The present invention discloses an electrospun fibrous membrane with a significantly improved mechanical property. By providing reinforcing thread sets on the electrospun fibrous membrane body to impart the electrospun fibrous membrane with a greater mechanical property, the mechanical strength required for the movement of the tissue is ensured, and the electrospun fibrous membrane is easy to be folded or rolled into other shapes. The electrospun fibrous membrane body may be made of degradable materials, which are gradually degraded and absorbed in the process of inducing new tissue formation, thereby providing space for the formation of new tissues and reducing or avoiding permanent residue of the materials. At the same time, by subjecting the auxiliary thread to twisting treatment and controlling its twist, the reinforced electrospun fibrous membrane is endowed with good adhesiveness in addition to a good mechanical property, and the two materials in the resulting membrane are well adhered, integrated and non-detached, without causing any discomfort after implantation in the human body.

BRIEF DESCRIPTION OF THE DRAWINGS

The accompanied drawings, which are incorporated in and constitute a part of the specification, illustrate exemplary embodiments, features and aspects of the present invention together with the specification, and are used to explain the principle of the present invention.

DETAILED DESCRIPTION

The reinforced electrospun fibrous membrane of the present invention will be further described below according to some specific embodiments. Specific Examples are to further illustrate the present invention in detail, but the scope of the present invention is not limited thereto.

EXAMPLE 1

Figure 1:
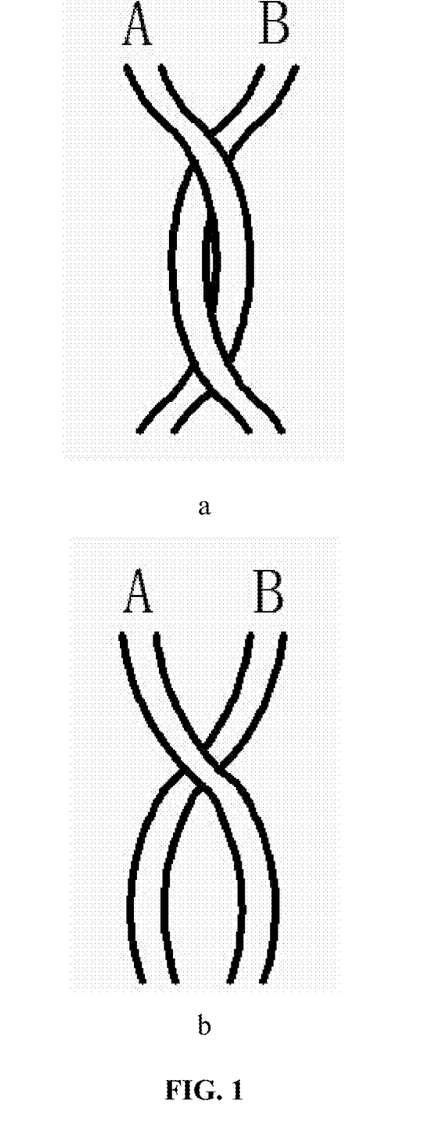
FIG. 1 is a schematic diagram for interlaced or crossed main thread and the auxiliary thread; a is a schematic diagram for interlacing of threads A and B, and b is a schematic diagram for crossing of threads A and B.
Figure 2:
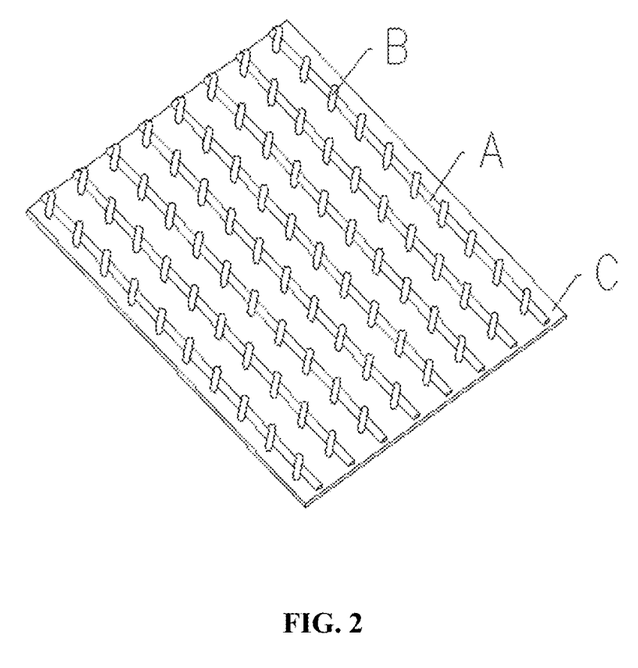
FIG. 2 is a structural schematic diagram for the reinforced electrospun fibrous membrane of the present invention, wherein A and B are main thread and auxiliary thread respectively, and C is an electrospun fibrous membrane body.

A reinforced electrospun fibrous membrane, as shown in FIG. 2, comprised an electrospun fibrous membrane body and a plurality of reinforcing thread sets fixed to the electrospun fibrous membrane body via through holes thereon, wherein each of the reinforcing thread sets was parallel to each other; each of the reinforcing thread sets comprised a starting end and a terminal end, both being connected to an edge of the electrospun fibrous membrane body; the reinforcing thread sets comprised one reinforcing fibrous thread consisting of a main thread and an auxiliary thread respectively arranged at a front side and a bottom side of the electrospun fibrous membrane body and configured to interlace each other at the through hole.

The auxiliary thread was subjected to twisting treatment at a twist of 10 to 100.

Figure 3:
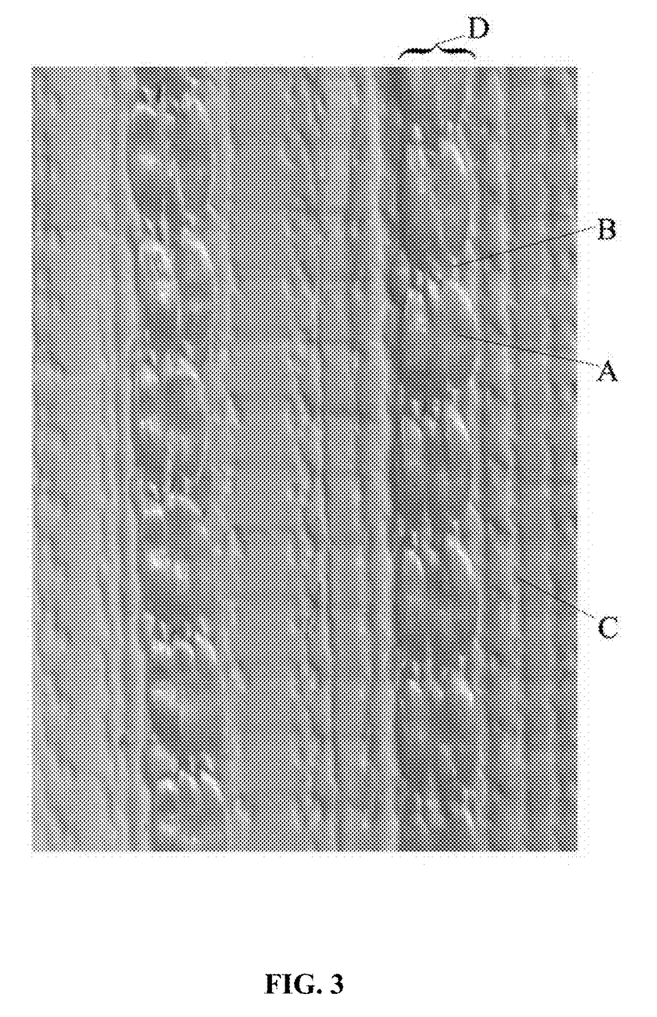
FIG. 3 is a front view of the reinforced electrospun fibrous membrane of the present invention.
Figure 4:
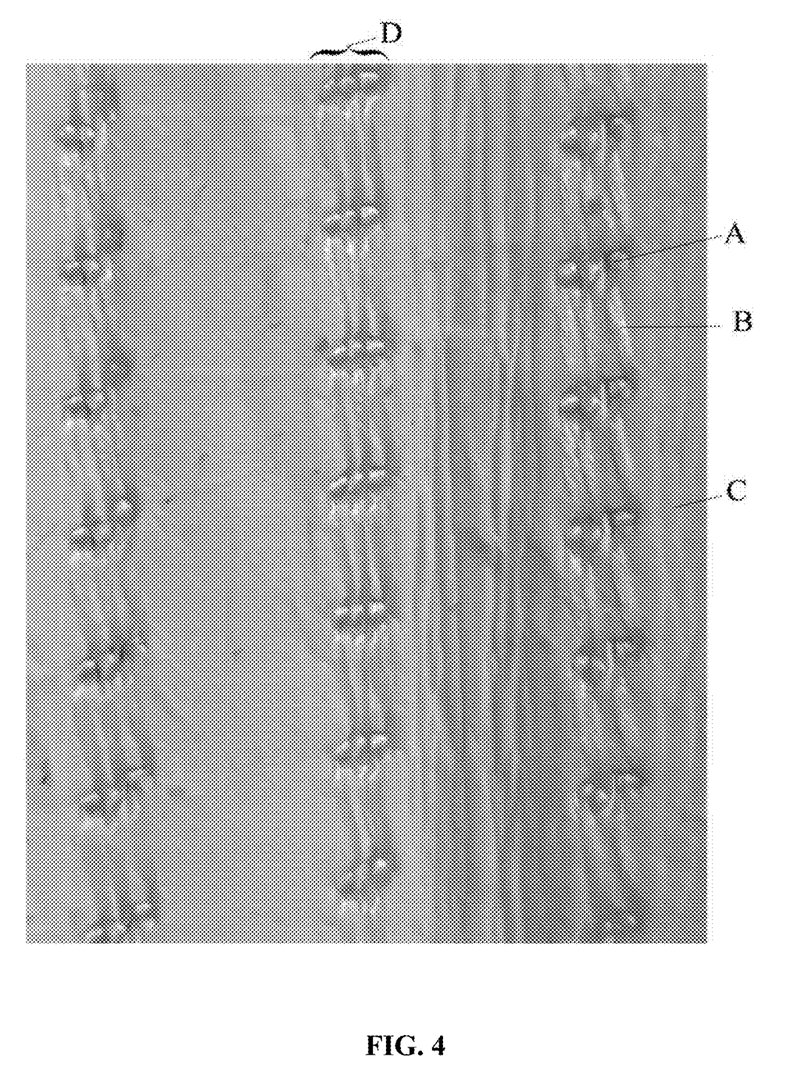
FIG. 4 is a rear view of the reinforced electrospun fibrous membrane of the present invention.

FIG. 3 was a front view of the reinforced electrospun fibrous membrane of the present invention. FIG. 4 was a rear view of the reinforced electrospun fibrous membrane of the present invention. As shown in FIGS. 3 and 4, A and B were respectively a main thread and an auxiliary thread, and C was an electrospun fibrous membrane body, wherein both of the main thread A and the auxiliary thread B were made of multiple filaments. The main thread A and the auxiliary thread B constituted a reinforcing fibrous thread, three of which made up one reinforcing thread set D, and any two of reinforcing thread sets were parallel and in a straight line. Both of a starting end and a terminal end of the reinforcing thread set D were connected to an edge of the electrospun fibrous membrane body C and all of the reinforcing thread sets D extend in the same direction.

The main thread A and the auxiliary thread B of the reinforced electrospun fibrous membrane were fixed to the electrospun fibrous membrane body C by sewing, and were interlaced in the through hole so that they were distributed at both sides of the electrospun fibrous membrane body C, respectively. Moreover, it could be seen from FIGS. 3 and 4 that reinforcing fibrous threads were well adhered to the electrospun fibrous membrane body C.

EXAMPLE 2

A method of preparing the reinforced electrospun fibrous membrane according to Example 1, comprised steps of:

S1: preparing for an electrospun fibrous membrane body;

the electrospun fibrous membrane body was prepared as follows: an L-polylactic acid was selected and dissolved with hexafluoroisopropanol to prepare 20 percent by mass/volume (g/mL) of electrospun solution; the spun solution was added to a syringe, which was connected to the front tube of a micro-pump and the spinneret, and the following parameters were set: a spinning voltage 35 kv, solution propulsion velocity 10 ml/h, receiving distance 30 cm, and a rotate speed of a roller 400 r/min; electrostatic spinning was performed; the resulting electrospun fibrous membrane was placed in a blast air oven, dried at 50° C. for 5 h, and then soaked in 75% alcohol for 1 h and dried at 50° C. overnight in a drying oven to obtain a electrospun fibrous membrane body;

S2: preparing a main thread and an auxiliary thread;

the main thread was made by twisting 100 pieces of polylactic acid filaments with a diameter of 0.01 mm or less, and a twist of the main thread was 2;

the auxiliary thread was made by twisting 20 pieces of polylactic acid filaments with a diameter of 0.01 mm or less, and a twist of the auxiliary thread was 50; and S3: the main thread as an upper thread and the auxiliary thread as a bottom thread were fixed to the electrospun fibrous membrane body by means of sewing; a SINGER 9960 sewing machine was selected; multiple through holes were formed in the electrospun fibrous membrane body during sewing, and main threads and auxiliary threads were interlaced in through holes.

EXAMPLE 3

A method of preparing the reinforced electrospun fibrous membrane according to Example 1, comprised steps of:

S1: preparing for an electrospun fibrous membrane body by the same specific process as in Example 2;

S2: preparing a main thread and an auxiliary thread;

the main thread was made by twisting 100 pieces of UHMWPE filaments with a diameter of 0.01 mm or less, and a twist of the main thread was 20;

the auxiliary thread was made by twisting 20 pieces of polylactic acid filaments with a diameter of 0.01 mm or less, and a twist of the auxiliary thread was 10; and S3: the main thread as an upper thread and the auxiliary thread as a bottom thread are fixed to the electrospun fibrous membrane body by means of sewing; the specific process was the same as that of Example 2.

EXAMPLE 4

A method of preparing the reinforced electrospun fibrous membrane according to Example 1, comprised steps of:

S1: preparing for an electrospun fibrous membrane body by the same specific process as in Example 2;

S2: preparing a main thread and an auxiliary thread;

the main thread was made by twisting 100 pieces of UHMWPE filaments with a diameter of 0.01 mm or less, and a twist of the main thread was 20;

the auxiliary thread was made by twisting 20 pieces of polycaprolactone filaments with a diameter of 0.01 mm or less, and a twist of the auxiliary thread was 100; and S3: the main thread as an upper thread and the auxiliary thread as a bottom thread are fixed to the electrospun fibrous membrane body by means of sewing; the specific process was the same as that of Example 2.

EXAMPLE 5

A method of preparing the reinforced electrospun fibrous membrane according to Example 1, comprised steps of:

S1: preparing for an electrospun fibrous membrane body;

the electrospun fibrous membrane body was prepared as follows: a polycaprolactone was selected and dissolved with hexafluoroisopropanol to prepare 10 percent by mass/volume (g/mL) of electrospun solution; the spun solution was added to a syringe, which was connected to the front tube of a micro-pump and the spinneret, and the following parameters were set: a spinning voltage 10 kv, solution propulsion velocity 4 mL/h, receiving distance 20 cm, and a rotate speed of a roller 800 r/min; electrostatic spinning was performed; the resulting electrospun fibrous membrane was placed in a blast air oven, dried at 40° C. for 10 h, and then soaked in 95% alcohol for 0.5 h and dried at 50° C. overnight in a drying oven to obtain a electrospun fibrous membrane body;

S2: preparing a main thread and an auxiliary thread;

the main thread was made by twisting 100 pieces of polycaprolactone filaments with a diameter of 0.01 mm or less, and a twist of the main thread was 5;

the auxiliary thread was made by twisting 20 pieces of polycaprolactone filaments with a diameter of 0.01 mm or less, and a twist of the auxiliary thread was 45; and S3: the main thread as an upper thread and the auxiliary thread as a bottom thread are fixed to the electrospun fibrous membrane body by means of sewing; a SINGER 9960 sewing machine was selected; multiple through holes were formed in the electrospun fibrous membrane body during sewing, and main threads and auxiliary threads were interlaced in through holes.

EXAMPLE 6

A method of preparing the reinforced electrospun fibrous membrane according to Example 1, comprised steps of:

S1: preparing for an electrospun fibrous membrane body by the same specific process as in Example 5;

S2: preparing a main thread and an auxiliary thread;

the main thread was made by twisting 100 pieces of polyethylene glycol terephthalate filaments with a diameter of 0.01 mm or less, and a twist of the main thread was 10;

the auxiliary thread was made by twisting 20 pieces of polylactic acid filaments with a diameter of 0.01 mm or less, and a twist of the auxiliary thread was 30; and S3: the main thread as an upper thread and the auxiliary thread as a bottom thread are fixed to the electrospun fibrous membrane body by means of sewing; the specific process was the same as that of Example 5.

EXAMPLE 7

A method of preparing the reinforced electrospun fibrous membrane according to Example 1, comprised steps of:

S1: preparing for an electrospun fibrous membrane body by the same specific process as in Example 5;

S2: preparing a main thread and an auxiliary thread;

the main thread was made by twisting 100 pieces of UHMWPE filaments with a diameter of 0.01 mm or less, and a twist of the main thread was 20;

the auxiliary thread was made by twisting 20 pieces of UHMWPE filaments with a diameter of 0.01 mm or less, and a twist of the auxiliary thread was 100; and S3: the main thread as an upper thread and the auxiliary thread as a bottom thread are fixed to the electrospun fibrous membrane body by means of sewing; the specific process was the same as that of Example 5.

EXAMPLE 8

A method of preparing the reinforced electrospun fibrous membrane according to Example 1, comprised steps of:

S1: preparing for an electrospun fibrous membrane body by the same specific process as in Example 5;

S2: preparing a main thread and an auxiliary thread;

the main thread was made by twisting 100 pieces of silk fiber filaments with a diameter of 0.01 mm or less, and a twist of the main thread was 8;

the auxiliary thread was made by twisting 20 pieces of silk fiber filaments with a diameter of 0.01 mm or less, and a twist of the auxiliary thread was 40; and S3: the main thread as an upper thread and the auxiliary thread as a bottom thread are fixed to the electrospun fibrous membrane body by means of sewing; the specific process was the same as that of Example 5.

EXAMPLE 9

A method of preparing the reinforced electrospun fibrous membrane according to Example 1, comprised steps of:

S1: preparing for an electrospun fibrous membrane body by the same specific process as in Example 5;

S2: preparing a main thread and an auxiliary thread;

the main thread was made by twisting 100 pieces of polyethylene glycol terephthalate filaments with a diameter of 0.01 mm or less, and a twist of the main thread was 20;

the auxiliary thread was made by twisting 20 pieces of polyethylene glycol terephthalate filaments with a diameter of 0.01 mm or less, and a twist of the auxiliary thread was 70; and S3: the main thread as an upper thread and the auxiliary thread as a bottom thread are fixed to the electrospun fibrous membrane body by means of sewing; the specific process was the same as that of Example 5.

COMPARATIVE EXAMPLE 1

A mechanical property test was made on the electrospun fibrous membrane body obtainable from the step S1 of Example 2.

COMPARATIVE EXAMPLE 2

A mechanical property test was made on the electrospun fibrous membrane body obtainable from the step S1 of Example 5.

COMPARATIVE EXAMPLE 3

A composite membrane A similar to the reinforced electrospun fibrous membrane of Example 1 in structure was prepared by the following method, comprising steps of:
S1: preparing for an electrospun fibrous membrane body by the same specific process as in Example 2;
S2: preparing a main thread and an auxiliary thread;
the main thread was made of 1 piece of UHMWPE filament with a diameter of 0.01 mm or less;
the auxiliary thread was made of 1 piece of polycaprolactone filament with a diameter of 0.01 mm or less;
neither the main thread nor the auxiliary thread was twisted; and
S3: the main thread as an upper thread and the auxiliary thread as a bottom thread are fixed to the electrospun fibrous membrane body by means of sewing; the specific process was the same as that of Example 2.

COMPARATIVE EXAMPLE 4

A composite membrane B similar to the reinforced electrospun fibrous membrane of Example 1 in structure was prepared by the following method, comprising steps of:
S1: preparing for an electrospun fibrous membrane body by the same technique in Example 2;
S2: preparing a main thread and an auxiliary thread;
the main thread was made of 100 pieces of UHMWPE filaments with a diameter of 0.01 mm or less;
the auxiliary thread was made of 20 pieces of polycaprolactone filaments with a diameter of 0.01 mm or less;
neither the main thread nor the auxiliary thread was twisted; and
S3: the main thread as an upper thread and the auxiliary thread as a bottom thread are fixed to the electrospun fibrous membrane body by means of sewing; the specific process was the same as that of Example 2.

COMPARATIVE EXAMPLE 5

A composite membrane C similar to the reinforced electrospun fibrous membrane of Example 1 in structure was prepared by the following method, comprising steps of:
S1: preparing for an electrospun fibrous membrane body by the same specific process as in Example 2;
S2: preparing a main thread and an auxiliary thread;
the main thread was made by twisting 100 pieces of UHMWPE filaments with a diameter of 0.01 mm or less, and a twist of the auxiliary thread was 5;
the auxiliary thread was made by twisting 20 pieces of polycaprolactone filaments with a diameter of 0.01 mm or less, and a twist of the auxiliary thread was 150; and S3: the main thread as an upper thread and the auxiliary thread as a bottom thread are fixed to the electrospun fibrous membrane body by means of sewing; the specific process was the same as that of Example 2.

COMPARATIVE EXAMPLE 6

A composite membrane D similar to the reinforced electrospun fibrous membrane of Example 1 in structure was prepared by the following method, comprising steps of:
S1: preparing for an electrospun fibrous membrane body by the same specific process as in Example 2;
S2: preparing a main thread and an auxiliary thread;
the main thread was made by twisting 100 pieces of UHMWPE filaments with a diameter of 0.01 mm or less, and a twist of the main thread was 20;
the auxiliary thread was made by twisting 20 pieces of polycaprolactone filaments with a diameter of 0.01 mm or less, and a twist of the auxiliary thread was 5; and
S3: the main thread as an upper thread and the auxiliary thread as a bottom thread are fixed to the electrospun fibrous membrane body by means of sewing; the specific process was the same as that of Example 2.

Tests for Mechanical Property and Adhesiveness

Test membranes included the reinforced electrospun fibrous membranes prepared according to the methods of Examples 2-9, the membranes A to D prepared according to the methods of Comparative Examples 3-6, and the electrospun fibrous membrane bodies obtained in Comparative Examples 1-2.

Maximum tensile force Fmax test: the above test membranes were subjected to a mechanical property test according to the standard of *EN ISO* 527-3 *Plastics—Determination of tensile properties—Part 3: Test conditions for films and sheet* to obtain the maximum tensile force Fmax of each of the test membranes.

Evaluation on adhesiveness: the adhesiveness of the above test membranes was evaluated by a visual inspection method and a tensile test method (the electrospun fibrous membrane body obtained in Comparative Examples 1-2 did not contain a composite reinforcing fibrous thread, and evaluation on adhesiveness was thus not made). Standard for evaluation by visual inspection was as below: 5 points were full marks, 5 indicated very good, 4 indicated good, 3 indicated ordinary, 2 indicated poor, 1 indicated very poor, 0 indicated that reinforcing fibrous threads cannot be composited with electrospun fibrous membrane body; a tensile test referred to stretching a test membrane as a whole with a 100N tensile force, and the tensile direction was the same as the extension direction of the reinforcing fibrous thread. If the reinforcing fibrous thread was well adhered to the electrospun fibrous membrane body, the electrospun fibrous membrane body would not be torn under a tensile force; if the reinforcing fibrous thread was not well adhered to the electrospun fibrous membrane body, the electrospun fibrous membrane body would be easily torn under a tensile force.

Test results of mechanical property and adhesiveness were as follows:

|  | Max. Tensile Force Fmax (N) | Evaluation on Adhesiveness | |
|---|---|---|---|
|  |  | Visual Inspection | Whether electrospun fibrous membrane body is torn under a tensile force of 100N |
| Example 2 | 1200 | 5 | No |
| Example 3 | 1700 | 4 | No |
| Example 4 | 1650 | 3 | No |
| Example 5 | 1000 | 5 | No |
| Example 6 | 1500 | 5 | No |
| Example 7 | 2200 | 3 | No |
| Example 8 | 850 | 5 | No |
| Example 9 | 1100 | 4 | No |
| Comparative Example 1 | 5N | — | — |
| Comparative Example 2 | 8N | — | — |
| Comparative Example 3 | * | 0 | Reinforcing fibrous thread cannot be composited with electrospun fibrous membrane body. |
| Comparative Example 4 | * | 0 | Reinforcing fibrous thread cannot be composited with electrospun fibrous membrane body. |
| Comparative Example 5 | * | 0 | Reinforcing fibrous thread cannot be composited with electrospun fibrous membrane body. |
| Comparative Example 6 | * | 0 | Reinforcing fibrous thread cannot be composited with electrospun fibrous membrane body. |

\* indicated that Reinforcing fibrous thread cannot be composited with electrospun fibrous membrane body so that this datum cannot be measured.
— indicated absence of this datum.

The foregoing descriptions are merely specific embodiments of the present invention, but the protection scope of the present invention is not limited thereto. Any changes or substitutions within the technical scope disclosed in the present invention, which are readily conceived of by a person skilled in the art, should be covered by the protection scope of the present invention. Therefore, the protection scope of the present invention should be subject to the protection scope of the claims.

Practicability

A reinforced electrospun fibrous membrane and a preparation method thereof according to the Examples of the present invention are applicable to the biomedical field, particularly suitable for the preparation of materials for repair of human body, for example, preparation of bionic ligaments or bionic tendons and the like. The reinforced electrospun fibrous membrane of the invention can effectively improve the mechanical properties of the electrospun fibrous membrane. By providing reinforcing thread sets on the electrospun fibrous membrane body to impart the electrospun fibrous membrane with a greater mechanical property, the mechanical strength required for the movement of the tissue is ensured, and the electrospun fibrous membrane is easy to be folded or rolled into other shapes. The electrospun fibrous membrane may be made of degradable materials, which are gradually degraded and absorbed in the process of inducing new tissue formation, thereby providing space for the formation of new tissues and reducing or avoiding permanent residue of the materials.

At the same time, by subjecting the auxiliary thread to twisting treatment and controlling its twist, the reinforced electrospun fibrous membrane is endowed with good adhesiveness in addition to a good mechanical property, and the two materials in the resulting membrane are well adhered, integrated and non-detached, without causing any discomfort after implantation in the human body.

The invention claimed is:

1. An electrospun fibrous membrane, comprising an electrospun fibrous membrane body and a plurality of parallel reinforcing thread sets fixed to the electrospun fibrous membrane body via through holes thereon, wherein:

each of the reinforcing thread sets comprises a starting end and a terminal end, both being connected to an edge of the electrospun fibrous membrane body;

each of the reinforcing thread sets comprises at least one reinforcing fibrous thread comprising a main thread and an auxiliary thread each arranged at both a front side and a bottom side of the electrospun fibrous membrane body, and wherein the main thread and the auxiliary thread are interlaced with each other at the through holes; and the auxiliary thread has 10 to 100 twists.

2. The electrospun fibrous membrane of claim 1, wherein each of the main threads and/or the auxiliary threads is made of at least two filaments with a diameter of 0.01 mm or less.

3. The electrospun fibrous membrane of claim 2, wherein each of the filaments is a silk fiber, a polyester fiber, an ultra high molecular weight polyethylene fiber, a polylactic acid fiber or a polycaprolactone fiber.

4. The electrospun fibrous membrane of claim 1, wherein each of the reinforcing thread sets contains at least two reinforcing fibrous threads.

5. The electrospun fibrous membrane of claim 1, wherein an extension direction of the reinforcing thread sets is the same as a length or width direction of the electrospun fibrous membrane body.

6. The electrospun fibrous membrane of claim 1, wherein a fiber distribution of the electrcospun fibrous membrane body is subjected to orientation and an extension direction of the reinforcing thread sets is the same as the fiber orientation direction of the electrospun fibrous membrane body.

7. The electrospun fibrous membrane of claim 1, wherein the electrospun fibrous membrane body has a thickness of 0.2 to 2 mm.

8. The electrospun fibrous membrane of claim 1, wherein a distance between two adjacent reinforcing thread sets is from 2 to 25 mm.

9. The electrospun fibrous membrane of claim 1, wherein the electrospun fibrous membrane body is composed of a degradable material.

10. The electrospun fibrous membrane of claim 9, wherein the degradable material is any one of or a mixture of two or more selected from the group consisting of polyurethane, polylactic acid, polycaprolactone, polyglycolic acid, polymethylmethacrylate, chitosan, lactic acid-glycolic acid copolymer, alginic acid, alginate, collagen, gelatin, chondroitin, hyaluronic acid, fibrin, and modified cellulose.

11. The electrospun fibrous membrane of claim 1, wherein the electrospun fibrous membrane body contains a bioactive factor.

12. The electrospun fibrous membrane of claim 11, wherein the bioactive factor is any one of or a mixture of two or more selected from the group consisting of a platelet growth factor, a basic fibroblast growth factor, a bone growth factor, a vascular endothelial growth factor, a connective tissue growth factor and a glial growth factor.

13. The eiectrospun fibrous membrane of claim 1, wherein each of the reinforcing thread sets is in a straight line as a whole.

14. A method of preparing the electrospun fibrous membrane of claim 1, comprising the steps of:

S1: preparing an electrospun fibrous membrane body;

S2: preparing a main thread and an auxiliary thread; and

S3: fixing the main thread and the auxiliary thread to the electrospun fibrous membrane body through sewing.

15. The method of claim 14, wherein the step S1 comprises steps of:
S11: preparing an electrospun solution, in which a polymer has a concentration of 5 to 20 percent by mass/volume; and
S12: setting ranges of parameters for electrostatic spinning that include: spinning voltage: 10 kv to 50 kv; solution propulsion velocity: 2.5 mL/h to 10 mL/h; receiving distance: 10 cm to 30 cm; rolling speed of a receiver: 400 to 2000 r/min; and subjecting the above electrospun solution to electrostatic spinning to obtain the electrospun fibrous membrane body.

16. The method of claim 15, further comprising spraying a bioactive factor during the electrostatic spinning.

17. A method of repair of a human body, comprising implanting the electrospun fibrous membrane of claim 1 in the human body.

18. A bionic ligament or bionic tendon made of the electrospun fibrous membrane of claim 1.

19. The bionic ligament or bionic tendon of claim 18, prepared by rolling the electrospun fibrous membrane into a tubular shape and then securing the rolled membrane by sewing.

* * * * *